US 10,610,628 B2

(12) United States Patent
Hobro

(10) Patent No.: US 10,610,628 B2
(45) Date of Patent: Apr. 7, 2020

(54) DIALYSIS MONITORS, METHODS RELATING TO HEATING OF FLUIDS, AND USE OF BATTERY UNITS OF DIALYSIS MONITORS

(71) Applicant: GAMBRO LUNDIA AB, Lund (SE)

(72) Inventor: Sture Hobro, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 755 days.

(21) Appl. No.: 15/034,247

(22) PCT Filed: Nov. 11, 2014

(86) PCT No.: PCT/EP2014/074240
§ 371 (c)(1),
(2) Date: May 4, 2016

(87) PCT Pub. No.: WO2015/071247
PCT Pub. Date: May 21, 2015

(65) Prior Publication Data
US 2016/0279313 A1  Sep. 29, 2016

(30) Foreign Application Priority Data
Nov. 13, 2013  (SE) ........................ 1351341

(51) Int. Cl.
*A61M 1/16* (2006.01)
*A61L 2/04* (2006.01)
(52) U.S. Cl.
CPC .............. *A61M 1/1662* (2014.02); *A61L 2/04* (2013.01); *A61M 1/16* (2013.01); *A61M 1/166* (2014.02);
(Continued)

(58) Field of Classification Search
CPC .. A61M 1/1662; A61M 1/166; A61M 1/1664; A61M 1/16; A61M 1/1686; A61L 12/04
See application file for complete search history.

(56) References Cited

U.S. PATENT DOCUMENTS 4,122,010 A   10/1978  Riede et al.
5,624,572 A    4/1997  Larson et al.
(Continued)

FOREIGN PATENT DOCUMENTS

CN      1382498      12/2002
CN      2877693       3/2004
(Continued)

OTHER PUBLICATIONS

Search Report for International Patent Application PCT/EP2014/074240 dated Jan. 27, 2015 (4 pages).
(Continued)

*Primary Examiner* — Ariana Zimbouski
(74) *Attorney, Agent, or Firm* — K&L Gates LLP

(57) ABSTRACT

A dialysis monitor with a treatment fluid path configured to provide treatment fluid to a dialyzer when dialysis treatment is performed by the dialysis monitor is provided. A battery unit is connected to a controller and at least a portion of the functional elements of the dialysis monitor in order to provide back-up power should the supply of external power be discontinued. Energy of the battery unit is used to provide energy to the heater in preparation for and/or at least partly during thermal disinfection of the treatment fluid path or when starting up the preparation of treatment fluid thereby shortening the time required for the thermal disinfection and the starting up of the preparation of treatment fluid, respectively.

18 Claims, 5 Drawing Sheets

(52) U.S. Cl.
CPC ........ *A61M 1/1664* (2014.02); *A61M 1/1686*
(2013.01); *A61L 2202/24* (2013.01); *A61M 2205/3368* (2013.01); *A61M 2205/36* (2013.01); *A61M 2205/8206* (2013.01)

(56) References Cited

U.S. PATENT DOCUMENTS

| | | | |
|---|---|---|---|
| 2004/0031756 A1 | 2/2004 | Suzuki et al. | |
| 2009/0206023 A1* | 8/2009 | Rohde | A61M 1/16 210/321.71 |
| 2010/0022937 A1* | 1/2010 | Bedingfield | A61M 1/16 604/6.09 |
| 2012/0168426 A1 | 7/2012 | Hedmann et al. | |
| 2012/0248039 A1 | 10/2012 | Rohde et al. | |
| 2013/0158469 A1 | 6/2013 | Hopping et al. | |

FOREIGN PATENT DOCUMENTS

| | | |
|---|---|---|
| CN | 102895711 | 1/2013 |
| JP | 2012217943 | 11/2012 |
| WO | 9609080 | 3/1996 |
| WO | 2011/000371 | 1/2011 |
| WO | 2014/150626 | 9/2014 |

OTHER PUBLICATIONS

Written Opinion for International Patent Application PCT/EP2014/074240 dated Jan. 27, 2015 (6 pages).

* cited by examiner

DIALYSIS MONITORS, METHODS RELATING TO HEATING OF FLUIDS, AND USE OF BATTERY UNITS OF DIALYSIS MONITORS

PRIORITY CLAIM

The present application is a National Phase of International Application No. PCT/EP2014/074240, filed on Nov. 11, 2014, which claims priority to Swedish Patent Application No. 1351341-1, filed Nov. 13, 2013, the entire contents of each of which are incorporated herein by reference and relied upon.

TECHNICAL FIELD

The present invention relates to dialysis monitors configured to supply energy from a battery unit to a heating element in order to heat fluid in a treatment fluid path at a time when dialysis treatment is not being performed by the dialysis monitor on a patient. The present invention also relates to related methods and the use of a battery unit of a dialysis monitor.

BACKGROUND

There are several types of treatments in which blood is extracted in an extracorporeal blood circuit. Such treatments involve, for example, haemodialysis, haemofiltration, haemodiafiltration, plasmapheresis, blood component separation, blood oxygenation, etc. Normally, blood is removed from a blood vessel at an access site and returned to the same blood vessel or at another location in the body.

In for example the cases of haemodialysis, haemofiltration, haemodiafiltration, and plasmapheres, but not limited to these cases, a treatment fluid (also referred to as a dialysis fluid) is made approximately isotonic with a patient's blood. The treatment fluid and the patient's blood are made to flow on each side of a semi-permeable membrane of a membrane device (referred to as a dialyzer). Diffusive transfer is achieved from one side of the membrane to the other when the concentration of the substance on each side of the membrane differs. Such substances may be impurities in the blood (urea, creatinine, etc.) which thereby migrates from the blood to the treatment fluid. Since fluid normally has to be removed from the patient during haemodialysis, a convective transfer by ultrafiltration, resulting from a pressure difference created between the blood side and the treatment fluid side of the membrane, is added to the diffusive transfer.

An apparatus for extracorporeal blood treatment includes a treatment control monitor (dialysis monitor) which is connected to a disposable extracorporeal blood circuit. The disposable extracorporeal blood circuit includes blood transport lines (in general an arterial line for blood removal from the patient, and a venous line for blood return to the patient) and the membrane device for blood treatment.

The semi-permeable membrane of the membrane device divides a blood compartment, connected to the blood transport lines, and a fluid compartment, connected to treatment fluid supply and discharge circuits. The blood transport lines are further coupled to a sensor and actuator system equipped on the treatment control monitor, which system normally comprises means for blood circulation, pressure sensors, air bubble sensor, one or more circuit blocking clamps, blood detector, etc.

The treatment fluid supply circuit receives purified water from a water supply system. The water system may be a small unit providing water to only a single treatment control monitor but may also be a large unit providing water by means of a water system loop arrangement to a significant number of treatment units in for example a hospital or a clinic.

Dialysis fluid, which may come into contact with the patients' blood, is often prepared from the purified water by means of a treatment fluid supply circuit. It is of paramount importance that the dialysis fluid used for the treatment is free from virus, fungi, bacteria and their residue and degradation products, such as endotoxins.

Therefore, the treatment fluid path of a dialysis monitor may be disinfected between dialysis treatments in order to reduce the presence of virus, fungi, bacteria, etc in the treatment fluid path. Chemical disinfection (e.g. using NaOCl or other chemical disinfection agents) is an efficient way to reduce the presence of bacteria, etc but it makes great demands on the following rinse procedure and requires very close measuring to assure that the treatment fluid path is free of chemical residual products before being used for subsequent treatments. The chemical process is not environmentally friendly and may have a negative effect on the life-length of the disinfected parts and components.

In an alternative disinfection process, thermal disinfection is achieved by letting hot water pass through the treatment fluid path. As a result, the problem of chemical residual products does not exist, the process puts less load on the environment, and has comparatively less negative effect on the life-length of the disinfected parts and components.

Thermal disinfection of a monitor is preferably carried out after the treatment of each patient. As the number of dialysis patients increases there is a need to increase the available time for treatments in the clinics. Consequently, there is a desire to reduce the time spent on disinfection between treatments.

Furthermore, before dialysis treatment can be commenced for a patient, the dialysis monitor needs a certain time to start up the production of treatment fluid with the correct composition and set temperature. Again, as the number of dialysis patients increases there is a need to increase the available time for treatments in the clinics. Consequently, there is a need to reduce the time spent on the starting-up of, or preparation of, the treatment fluid before the dialysis treatment can be commenced on the patient.

SUMMARY

According to an aspect of the present invention there is provided a dialysis monitor for performing dialysis treatment on a patient, which comprises a treatment fluid path configured to provide treatment fluid to a dialyzer when dialysis treatment is performed by the dialysis monitor, a heater configured to heat fluid present in the treatment fluid path, a controller, and a battery unit, the battery unit being configured to provide back-up power to at least a portion of the dialysis monitor should the supply of external power be discontinued. The dialysis monitor further comprises a first switch connected between the battery unit and the heater, the first switch having a first state where energy is supplied from the battery unit to the heater and a second state where energy is substantially prevented from being supplied from the battery unit to the heater, and the controller is programmed to control the state of the first switch and to set the state of the first switch to the first state, thereby supplying energy from the battery unit to the heater, at a time when dialysis treatment is not being performed on a patient by the dialysis monitor.

According to another aspect of the present invention, the controller of the dialysis monitor referred to above is programmed to set the state of the first switch to the first state at the time of preparing for and/or at least partly during thermal disinfection of at least a portion of the treatment fluid path thereby using energy from the battery unit for heating fluid used for thermal disinfection.

According to another aspect of the present invention, the controller of the dialysis monitor referred to above is programmed to set the state of the first switch to the first state at a time when the dialysis monitor is starting up the preparation of treatment fluid thereby using energy from the battery unit for heating fluid towards and/or to a temperature to be used during dialysis treatment.

According to another aspect of the present invention, a method of providing energy to a fluid present in a treatment fluid path of a dialysis monitor is provided, where the dialysis monitor comprises a treatment fluid path configured to provide treatment fluid to a dialyzer when dialysis treatment is performed on a patient, a heater configured to heat fluid in the treatment fluid path, and a battery unit configured to provide back-up power to at least a portion of the dialysis monitor should the supply of external power be discontinued. The method comprises the step of providing energy from the battery unit to the heater at a time when dialysis treatment is not being performed on a patient by the dialysis monitor.

According to another aspect of the present invention, in the method referred to above, the step of providing energy from the battery unit to the heater comprises providing energy from the battery unit to the heater for heating fluid used for thermal disinfection at the time of preparing for and/or at least partly during thermal disinfection of at least a portion of the treatment fluid path. The method further comprises the step of enabling the heated fluid to flow through the treatment fluid path to perform thermal disinfection of at least a portion of the treatment fluid path.

According to another aspect of the present invention, in the method referred to above, the step of providing energy from the battery unit to the heater comprises providing energy from the battery unit to the heater for heating fluid towards and/or to a temperature to be used during dialysis treatment at a time when the dialysis monitor is starting up the preparation of treatment fluid.

According to another aspect of the present invention, a back-up battery unit of a dialysis monitor is used for providing power to a heating element in order to heat fluid in a treatment fluid path at a time when dialysis treatment is not being performed on a patient by the dialysis monitor.

According to another aspect of the present invention, in the use of a back-up battery unit referred to above, the fluid heated in the treatment fluid path by means of energy from the back-up battery unit is used for the thermal disinfection of at least a portion of the treatment fluid path.

According to another aspect of the present invention, in the use of a back-up battery unit referred to above, the fluid heated in the treatment fluid path by means of energy from the back-up battery unit is used in the preparation of treatment fluid at a time when the dialysis monitor is starting up the preparation of treatment fluid.

An advantage of at least some embodiments of the present invention is that the power provided to the heater by means of the external power supply and the battery unit may exceed the maximum power available from the external power supply, which in turn, leads to a quick heating of the fluid to be used for thermal disinfection of the treatment fluid path or heating of the treatment fluid when starting up the preparation of treatment fluid.

Another advantage, at least in respect of some embodiments of the present invention, is that thermal disinfection of the dialysis monitor can be achieved in a short period of time. This in turn makes the time-between-treatments shorter since the time-between treatment is dependent on the time required for thermal disinfection. The short period of time is achieved by the use of the battery unit, possibly combined with power from the electrical system (external power supply/mains), for heating fluid to be used during thermal disinfection.

Yet another advantage, at least in respect of some embodiments of the present invention, is that starting up the preparation of treatment fluid can be achieved in a short period of time. This in turn makes the time-between-treatments shorter since the time-between treatment is dependent on the time required to starting up the preparation of treatment fluid. The short period of time is achieved by the use of the battery unit for heating fluid to a suitable temperature (close to body temperature e.g. 37° C.).

Consequently, there is the advantage of a more efficient use of the dialysis monitors (e.g. measured in percentage of time available for dialysis treatment of patients at for example clinics and hospitals). The working hours of the operating staff (nurses and technicians, as the case may be, who operate the dialysis monitors) can be shortened which in turn has positive economic effects for the clinics/hospitals and also positive work environmental effects for the operating staff. Patients also benefit as the dialysis monitors are used more efficiently.

DETAILED DESCRIPTION

Figure 1:
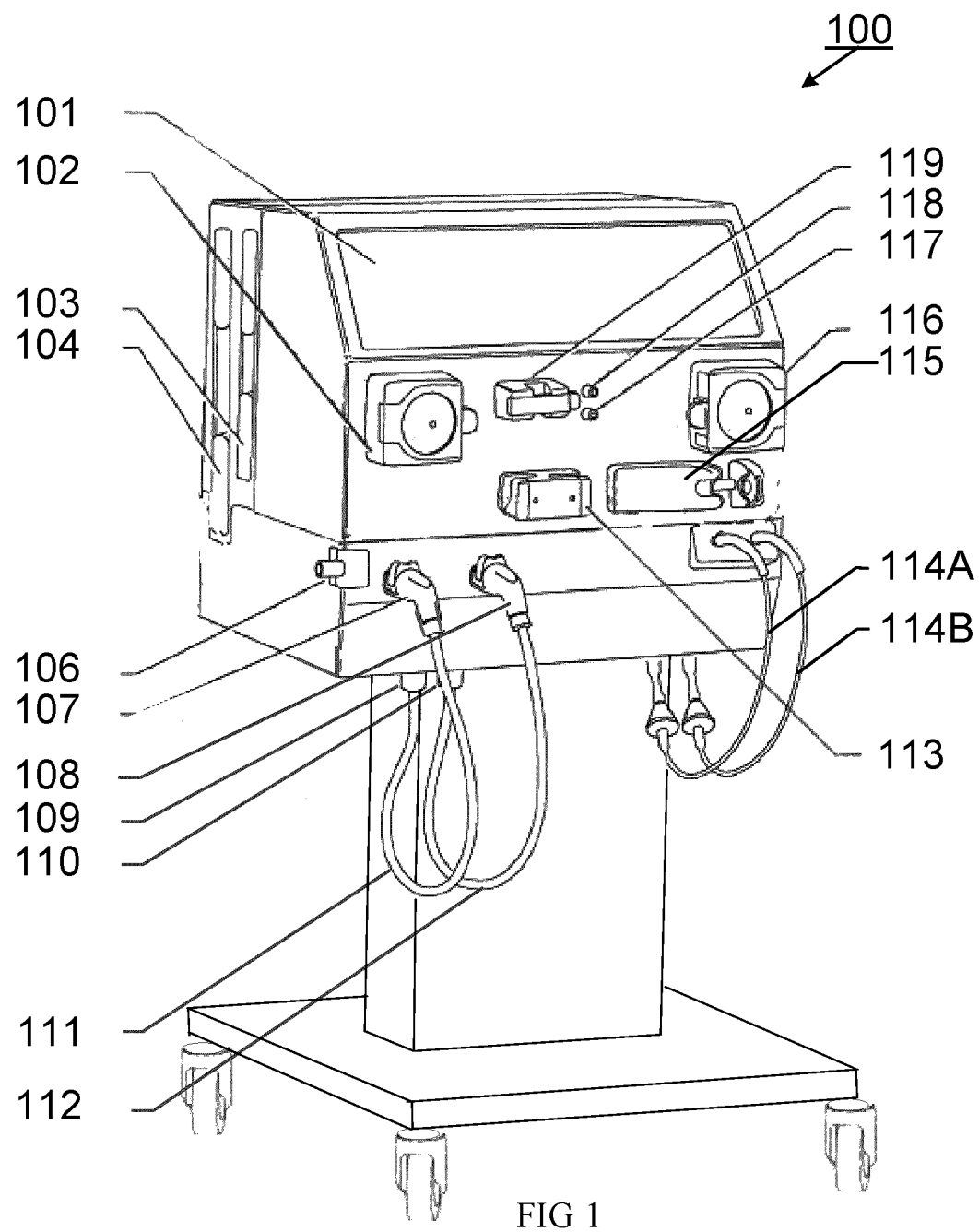
FIG. 1 depicts a dialysis monitor according to an embodiment of the present invention.
Figure 2:
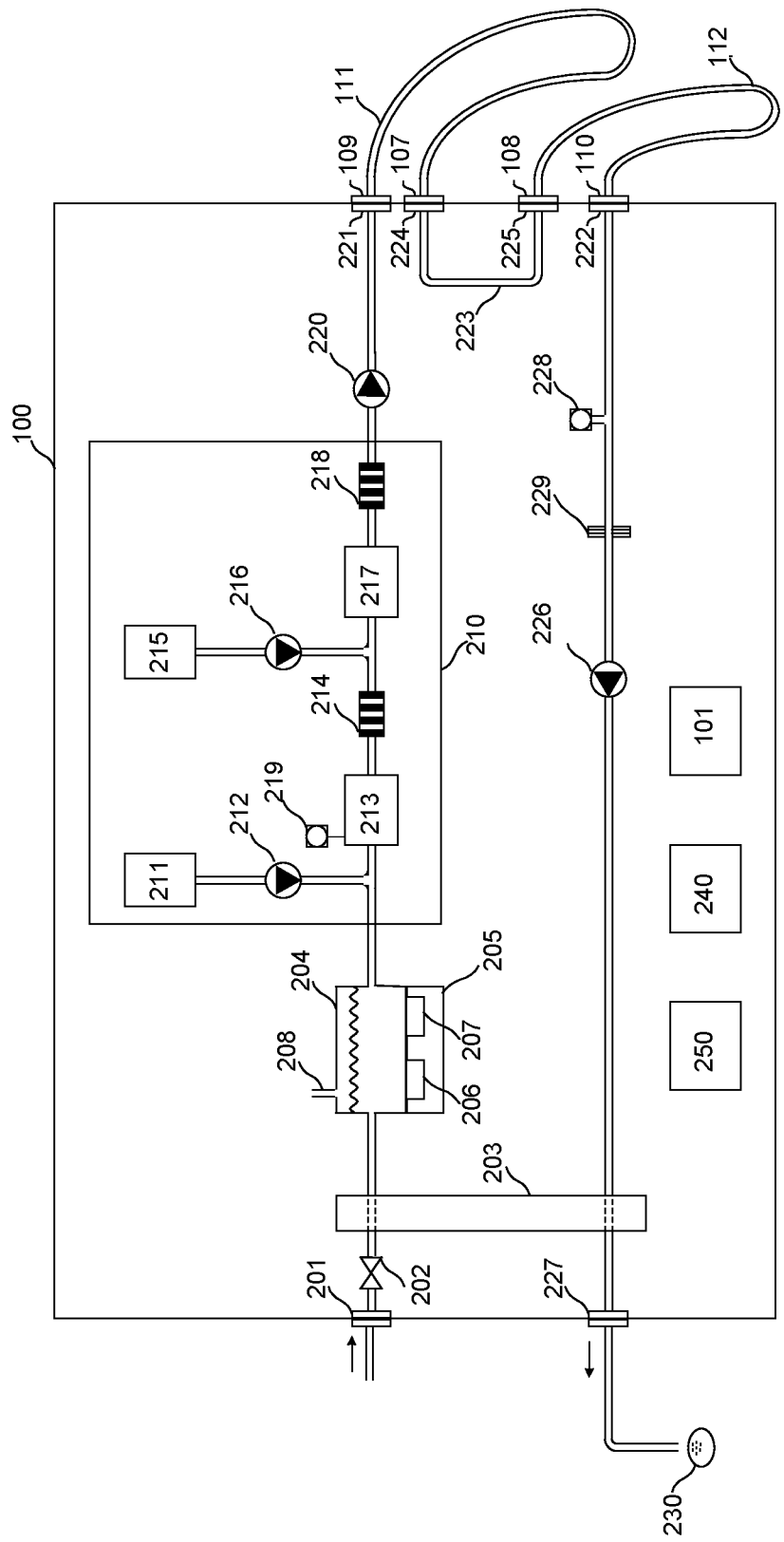
FIG. 2 shows a simplified schematic diagram of the treatment fluid path of a dialysis monitor according to an embodiment of the present invention.

FIG. 1 illustrates a Dialysis Monitor 100 according to an embodiment of the present invention and FIG. 2 shows a simplified schematic diagram of the Treatment Fluid Path of the Dialysis Monitor.

The Dialysis Monitor 100 comprises an Arterial Blood Pump 116 and a Venous Blood Pump 102, which may be peristaltic pumps. The treatment Control Monitor 100 further comprises a Venous Drip Chamber Holder 119, a First Pressure Sensor Input Port 117, a Second Pressure Sensor Input Port 118, a Membrane Device Holder 106 to which the membrane device (dialyzer) (not shown) can be mounted, a Blood Detector and Clamp Device 113, and a User Interface 101 (for displaying and entering of information to and from a user) as well as other components required to carry out the desired treatments (for example, a Syringe Pump 115) and possibly to manage disinfection by disinfection agents.

The Treatment Fluid Path is mainly located within the Dialysis Monitor. However, as is seen in FIG. 1, some components of the Treatment Fluid Path are accessible from the outside of the Dialysis Monitor. The Dialysis Monitor comprises a First Dry Concentrate Connector 104, a Second Dry Concentrate Connector 103 and an A Pick-Up Tube 114A and a B Pick-Up Tube 114B. FIG. 1 also shows the tubes (Treatment Fluid Supply Tube 111 and Treatment Fluid Return Tube 112) which are used to connect the Treatment Fluid Path to the dialyzer (not shown) when dialysis treatment is being performed. In FIG. 1, these tubes are "parked" at the Dialysis Monitor as will be explained more in detail in the following.

According to an embodiment of the present invention as is shown in FIG. 2, the upstream portion of the Treatment Fluid Path starts with an Inlet 201 which is configured to receive fluid from a water system (not shown). The Inlet is connected to a first side of an Inlet Valve 202 and the other side of the Inlet Valve is connected to an inlet on the first side of a Heat Exchanger 203. The outlet on the first side of the Heat Exchanger is connected to an inlet of a Tank 204. The Treatment Fluid Path further comprises a Heater 205 which is configured/arranged to heat fluid present in the Tank 204. The Heater in this particular embodiment is attached to the Tank and comprises a First Heating Element 206 and a Second Heating Element 207. Alternatively, the Heater may be located within the Tank or be located externally to the Tank (that is, as an in-line heater). The Tank is provided with an Expansion Exit 208 enabling air to escape the tank when fluid is entering the tank, and vice versa. The outlet of the Tank is connected to the inlet of a Treatment Fluid Mixing Unit 210.

The treatment fluid is prepared by a Treatment Fluid Mixing Unit 210 and the treatment fluid may be prepared from one or a number of concentrates and/or solutions provided in dry and/or fluid form supplied in, for example, canisters, bags, and/or containers.

FIG. 2 illustrates an example where the treatment fluid is prepared from A-concentrate which comprises all electrolytes except bicarbonate and B-concentrate which comprises bicarbonate. The A-Concentrate Container 211, which comprises the A-concentrate, is connected (e.g. by means of the A Pick-Up Tube 114A) to an inlet of an A-Pump 212. The outlet of the A-Pump is connected to the inlet of the Treatment Fluid Mixing Unit 210 (that is, the outlet of the Tank 204) and an inlet of a First Mixing Chamber 213. The outlet of the First Mixing Chamber is connected to an inlet of a First Conductivity Cell 214. The B-Concentrate Container 215, which comprises the B-concentrate, is connected (e.g. at the First Dry Concentrate Connector 104) to an inlet of a B-Pump 216. The outlet of the B-Pump is connected to the outlet of the First Conductivity Cell and an inlet of a Second Mixing Chamber 217. The outlet of the Second Mixing Chamber is connected to the inlet of a Second Conductivity Cell 218 and the outlet of the Second Conductivity Cell constitutes the outlet of the Treatment Fluid Mixing Unit. The temperature of the Treatment Fluid Path is normally measured by a Treatment Fluid Path Temperature Sensor 219 which in the present embodiment is co-located with the First Mixing Chamber 213 and is configured to measure the temperature of fluid in the First Mixing Chamber.

The outlet of the Treatment Fluid Mixing Unit 210 is connected to the inlet of a Flow Pump 220 and the outlet of the Flow Pump is connected to a Treatment Fluid Outlet 221. The path from the Inlet 201 to the Treatment Fluid Outlet 221 is referred to as the upstream portion of the Treatment Fluid Path.

During dialysis treatment, the Treatment Fluid Outlet 221 would be connected to the treatment fluid inlet (not shown) of the dialyzer (not shown) by means of a Treatment Fluid Supply Tube 111 thereby providing treatment fluid to the treatment fluid side of the semi-permeable membrane of the dialyzer as mentioned above. After having passed the dialyzer, the treatment fluid exits the dialyzer at an outlet (not shown) and it is returned by means of a Treatment Fluid Return Tube 112 to a Treatment Fluid Return Inlet 222 which constitutes the start of the downstream portion of the Treatment Fluid Path of the Dialysis Monitor.

The Treatment Fluid Supply Tube 111 is provided with a First Connector 109 which, when connected to the Dialysis Monitor 100, engages with the Treatment Fluid Outlet 221. Similarly, the Treatment Fluid Return Tube 112 is provided with a Second Connector 110 which, when connected to the Dialysis Monitor 100, engages with the Treatment Fluid Return Inlet 222.

At the time the dialyzer is not connected to the Treatment Fluid Path (which may for example be at the time of start-up of the Treatment Fluid Mixing Unit 210 or (re-)calibration thereof, after dialysis treatment, or during disinfection of the Treatment Fluid Path) the Treatment Fluid Supply Tube 111 and the Treatment Fluid Return Tube 112 may be connected together by means of a Bypass Conduit 223 provided in the Dialysis Monitor. In detail, the Bypass Conduit 223 is provided with a Supply Tube Parking Connector 224 and a Return Tube Parking Connector 225 at each end of the Bypass Conduit 223. The Treatment Fluid Supply Tube 111 is provided with a Third Connector 107 which, when connected to the Dialysis Monitor 100, engages with the Supply Tube Parking Connector 224. Similarly, the Treatment Fluid Return Tube 112 is provided with a Fourth Connector 108 which, when connected to the Dialysis Monitor 100, engages with the Return Tube Parking Connector 225.

The Treatment Fluid Return Inlet 222 is connected to the inlet of a Suction Pump 226 and the outlet thereof is connected to the inlet of the second side of the Heat Exchanger 203. The outlet of the second side of the Heat Exchanger is connected to an Exit 227. The Exit 227, which constitutes the end of the downstream portion of the Treatment Fluid Path of the Dialysis Monitor, is normally connected to a drain 230. A Pressure Sensor 228 and a Blood Leak Detector 229 may be located downstream the Treatment Fluid Return Inlet 222 as is shown in FIG. 2.

The Dialysis Monitor further comprises a Controller 240 and a User Interface 101. The Controller is operably connected to valves, heaters, pumps, thermometers, conductivity cells, pressure sensors, blood leak detectors, clamps, and other functional elements of the Dialysis Monitor, and is configured/programmed to read measured values and control the function of the functional elements. The Controller is further configured by means of analogue and/or digital circuits, and/or logic and/or micro-controllers, or similar, appropriately programmed by mean of software code, to carry out the functional steps of the operation of the Dialysis Monitors as disclosed in the various embodiments of the present invention. The Controller 240 is also connected to the User Interface 101, which may be a touch screen, in order to enable the displaying and entering of information to and from a user (not shown). It should be understood that certain activities, such as the starting, pausing and ending of dialysis treatment, the starting of disinfection of the Dialysis Monitor, etc., may be initiated by the user through the User Interface.

In operation, when dialysis treatment is performed by the Dialysis Monitor, the Controller 240 is programmed to set the Inlet Valve 202 in a fluidly open state. Water (normally pure water provided from a water system (not shown)) is thereby let in through the Inlet 201, the first side of the Heat Exchanger 203, into the Tank 204 and further into the Treatment Fluid Mixing Unit 210. In the Treatment Fluid Mixing Unit 210, A-concentrate from the A-Concentrate Container 211 is mixed into the Treatment Fluid Path by the Controller operating the A-Pump 212 and, after having been contained in the First Mixing Chamber 213, is let further through the First Conductivity Cell 214. The Controller is programmed to read the conductivity as measured by the First Conductivity Cell 214 and the measure is used by the Controller to calculate a control signal which it uses to control the A-Pump in order to arrive at a set mixture of A-concentrate and water. Similarly, B-Concentrate from the B-Concentrate Container 215 is mixed into the Treatment Fluid Path by the Controller operating the B-Pump 216 and, after having been contained in the Second Mixing Chamber 217, is let further through the Second Conductivity Cell 218. The Controller is programmed to read the conductivity as measured by the Second Conductivity Cell 214 and the measure is used by the Controller to calculate a control signal which it uses to control the B-Pump in order to arrive at a set mixture of B-concentrate in the treatment fluid, taking into account the A-concentrate already mixed with the water. The treatment fluid thereafter exits the Treatment Fluid Mixing Unit 210 and is moved forward in the Treatment Fluid Path by means of the Flow Pump 220 towards the Treatment Fluid Outlet 221.

The Controller 240 is programmed to read the temperature as measured by the Treatment Fluid Path Temperature Sensor 219 and to control the Heater 205 in order to arrive at a suitable temperature (close to body temperature e.g. 37° C.)

As mentioned above, at the time dialysis treatment is being performed, the Treatment Fluid Outlet 221 would be connected to the treatment fluid inlet (not shown) of the dialyzer (not shown) by means of the Treatment Fluid Supply Tube 111 thereby providing treatment fluid to the treatment fluid side of the semi-permeable membrane of the dialyzer. After having passed the dialyzer, the treatment fluid exits the dialyzer at the outlet (not shown) and it is returned by means of the Treatment Fluid Return Tube 112 to the Treatment Fluid Return Inlet 222.

The now used treatment fluid is moved forward by means of the Suction Pump 226 and, after having passed the Suction Pump, it flows through the second side of the Heat Exchanger 203 before it exits the Dialysis Monitor through the Exit 227. The Heat Exchanger allows the used treatment fluid, which has been heated to a temperature of approximately body temperature, to transfer heat over to the fresh water being received at the Inlet 201.

The highest priority for the Dialysis Monitor is that it operates in a, for the patient, safe way. This means that various incidents which may occur when dialysis treatment is being performed need to be managed by the Dialysis Monitor with minimum risk for the patient. One such incident that may occur is that the power supplied to the Dialysis Monitor through the mains (by means of an external power supply (not shown)) is lost when a patient is connected to the Dialysis Monitor and dialysis treatment is being performed. In order to manage such a situation, Dialysis Monitors may be equipped with a Battery Unit 250 (which may be referred to as an Uninterruptible Power Supply, UPS) which provides back-up power to at least parts of the Controller and, as may be controlled by the Controller, some functional elements of the Dialysis Monitor to at least place the Dialysis Monitor in a patient safe mode. The patient safe mode may include that the Controller is programmed to stop the dialysis fluid from flowing through the dialyzer whereas the blood is allowed to continue to be extracted and flow through the dialyzer and (if power is not restored within a certain period of time)/or, the Controller is programmed to stop all pumps and clamp the extracorporeal blood transport line(s) in order to prevent (further) blood from being extracted from the patient. It may also include providing an audio and/or visual alarm and enable a user to operate the Dialysis Monitor in order to return the already extracted blood present in the extracorporeal blood transport line(s) to the patient. The latter is performed by the Controller being programmed to run the Arterial and/or Venous Blood Pump(s) using power from the (back-up) Battery Unit in order to return as much blood as is possible to the patient. The Battery Unit 250, which normally is heavy, may be located in lower part of the Dialysis Monitor 100, such as in the foot or column (on which the fluid module is arranged).

Thermal disinfection can be carried out when dialysis treatment is not being performed. The dialyzer is then disconnected and the Third Connector 107 at the Treatment Fluid Supply Tube 111 is instead connected to the Supply Tube Parking Connector 224 and the Fourth Connector 108 at the Treatment Fluid Return Tube 112 is instead connected to the Return Tube Parking Connector 225. The upstream and downstream portions of the Treatment Fluid Path will thereby be connected together by means of the Bypass Conduit 223 and thermal disinfection of both portions of the Treatment Fluid Path will be possible by letting hot fluid through the Treatment Fluid Path. The hot fluid is created by the Controller 240 being programmed to control the Heater 205 to heat the fluid in the Tank 204 to a high temperature (for example 90° C.). The hot fluid is moved through the Treatment Fluid Path by the Controller operating the Flow Pump 220 and the Suction Pump 226. Heat of the fluid passing through the second side of the Heat Exchanger 203 will be transferred to the fluid entering the first side of the Heat Exchanger 203 thereby creating an energy efficient system.

Figure 3:
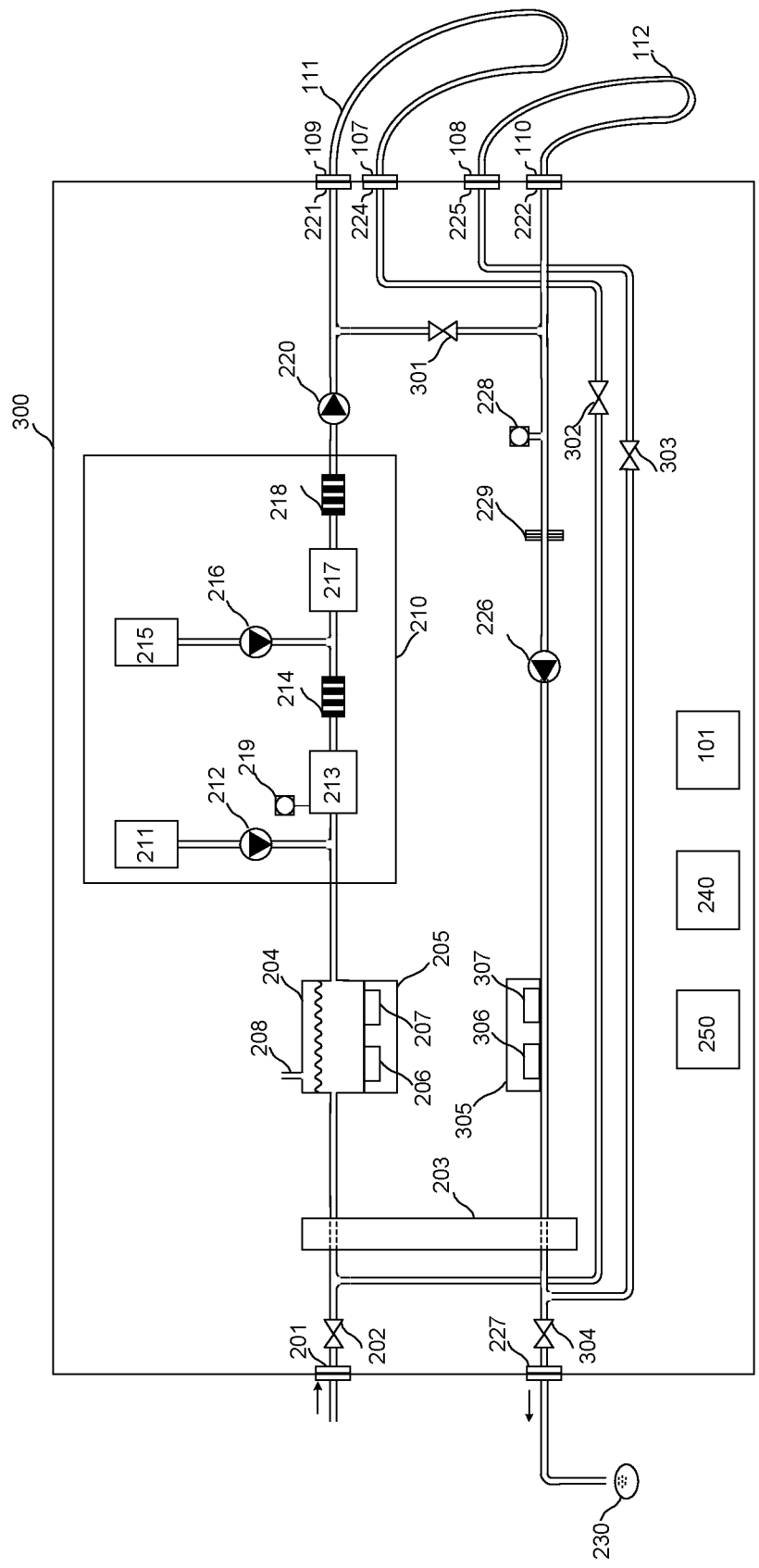
FIG. 3 shows a simplified schematic diagram of the treatment fluid path of a dialysis monitor according to an alternative embodiment of the present invention.

FIG. 3 shows a simplified schematic diagram of the treatment fluid path of a Dialysis Monitor 300 according to an alternative embodiment of the present invention. Elements corresponding to elements present in the schematic diagram of FIG. 2 have been labelled with the same reference numbers. It should be understood, though, that the Controller 240 may be programmed differently in order to enable it to carry out the functionality of the embodiments disclosed in relation to FIG. 3. The Treatment Fluid Path shown in FIG. 3 is designed to enable separate disinfection fluid loops for the upstream and downstream portions of the Treatment Fluid Paths, respectively. With reference to FIG. 3, the Treatment Fluid Outlet 221 is connected to the Treatment Fluid Return Inlet by means of a Bypass Valve 301. The Supply Tube Parking Connector 224 and the Return Tube Parking Connector 225 is no longer connected together by the Bypass Conduit 223. Instead, the Supply Tube Parking Connector 224 is connected to a first side of a First Return Valve 302. The second side of the First Return Valve 302 is connected to a location in between the Inlet Valve 202 and the inlet of the first side of the Heat Exchanger 203. The Return Tube Parking Connector 225 is connected to a first side of a Second Return Valve 303. The second side of the Second Return Valve 303 is connected to the outlet of the second side of the Heat Exchanger 203.

Additionally, an Exit Valve 304 is located between the outlet of the second side of the Heat Exchanger 203 and the Exit 227.

In operation, the Bypass Valve 301, when in a fluidly open state, allows the bypassing of the dialyzer (not shown), that is, the treatment fluid generated by the Treatment Fluid Mixing Unit 210 is led to the downstream portion of the Treatment Fluid Path. During dialysis treatment, the Bypass Valve 301 is in a fluidly closed state and the generated treatment fluid is led to the dialyzer (not shown) through the Treatment Fluid Outlet 221 and the Treatment Fluid Supply Tube 111.

At the time of disinfection, a first circulation loop is formed which includes at least a portion of the upstream portion of the Treatment Fluid Path. This is achieved by disconnecting the dialyzer (not shown), and instead connecting the Third Connector 107 at the Treatment Fluid Supply Tube 111 to the Supply Tube Parking Connector 224, fluidly open the First Return Valve 302, and fluidly close the Inlet Valve 202. A second circulation loop is formed which includes at least a portion of the downstream portion of the Treatment Fluid Path. This is achieved by disconnecting the dialyzer (not shown), and instead connecting the Fourth Connector 108 at the Treatment Fluid Return Tube 112 to the Return Tube Parking Connector 225, fluidly open the Second Return Valve 303, and fluidly close the Exit Valve 304. The Bypass Valve 301 is set in a fluidly closed state. Fluid used for disinfection can now be made to circulate in at least a portion of the relatively clean portion of the Treatment Fluid Path (upstream the dialyzer) while separated from fluid used for disinfection which is made to circulate in at least a portion of the relatively contaminated portion of the Treatment Fluid Path (downstream the dialyzer). The Flow Pump 220 and the Suction Pump 226 may be used to circulate the fluid in the first and second circulation loops, respectively. The fluid used for disinfection may be heated (thermal disinfection) and may comprise a disinfection and/or detergent agent.

In a variation to the above embodiment, a Second Heater 305 may be located and configured to heat fluid present in the downstream portion of the Treatment Fluid Path. The Second Heater 305 may comprise a First Heating Element of the Second Heater 306 and a Second Heating Element of the Second Heater 307. The Heater 205 and the Second Heater 305 may be used to heat fluid in the first and the second circulation loops, respectively.

According to an embodiment of the present invention, the Battery Unit 250 is used, when no dialysis treatment is being performed on a patient, to provide power to the Heater 205 in order to heat fluid in the Tank and/or the Treatment Fluid Path to a high temperature (for example 90° C.) in order to enable the hot fluid to perform thermal disinfection of at least a portion of the treatment fluid path, or at the starting up of preparation of treatment fluid.

According to an embodiment of the present invention, at the time of preparation for and/or at least partly during thermal disinfection of the Treatment Fluid Path (or at least a portion of the Treatment Fluid Path), energy is supplied from the Battery Unit 250 to the Heater 205 and/or the Second Heater 305 (if present). The heating of the fluid in the Tank and/or Treatment Fluid Path may be carried out very rapidly if energy is supplied from the Battery Unit 250 to the Heater 205 and/or the Second Heater 305 at the same time as energy is supplied from the mains (the external power supply) to the Heater 205 and/or the Second Heater 305. In this case, total energy provided to the Heater 205 and/or the Second Heater 305 from the mains and the Battery Unit 250 can be made to exceed the maximum power supply available to the Dialysis monitor from the mains alone.

The maximum power supply available from the mains is limited due to dimensions on power supply cables and related fuses and increasing the maximum power which can be supplied to a Dialysis Monitor in a clinic or hospital environment would often lead to unacceptable high reconstruction and operational costs. The rapid heating of the fluid to a sufficiently high temperature for thermal disinfection (for example 90° C.), which is made possible by the present invention, means that the time between treatments can be shortened as the time between treatments is very much dependent on the time for heating the fluid to a sufficiently high temperature.

Due to the high thermal capacity of the fluid used for thermal disinfection (e.g. water) and the volume needed to fill a dialysis fluid path the energy needed to heat the temperature from for example cold tap water to a temperature where thermal disinfection can be done is significant. The power available is restricted by the electrical system and the number of dialysis monitors connected to the same fuse. Without the power from the Battery Unit 250, it would take 5-15 minutes to reach the temperature required to perform thermal disinfection. With the power from the Battery Unit 250, as discussed above, this time is significantly reduced.

In an alternative embodiment of the present invention, which can be combined with any one of the disclosed embodiments, energy stored in the Battery Unit 250, is used to heat treatment fluid when the Dialysis Monitor is starting up the preparation of treatment fluid. In this case, the temperature of the treatment fluid can quickly be increased to a suitable temperature (close to body temperature e.g. 37° C.). That is, energy of the Battery Unit is used to heat the treatment fluid towards and/or to a temperature to be used during dialysis treatment. The starting up of the preparation of treatment fluid occurs at a time when the dialysis monitor is not performing dialysis treatment on a patient. The energy of the Battery Unit 250 may be used alone or in combination with energy from the externally provided electrical power (from the mains). At least in the latter case, the heating can be made quicker compared to only using externally provided electrical power since the externally provided electrical power is limited (due to installation, cable-dimensions, and maximum permitted current allowed by installed fuses).

In a variation of the present invention, energy from the Battery Unit is used to heat the treatment fluid to close to body temperature (at a location in the upstream portion of the Treatment Fluid Path) at least to a point of time when the temperature of the treatment fluid entering the second side of the Heat Exchanger 203 has a temperature which is in the range of the same temperature (e.g. at least 30° C.). At this point of time, fluid entering through the Inlet 201 will be heated in the Heat Exchanger by means of the transfer of energy from the second side to the first side thereof. An advantage of this variation of the present invention is that the power of the heater used during dialysis treatment (as supplied from the external power supply (mains)) can be made smaller (and thereby cheaper) as it, at any time, only needs to enhance the temperature of the fluid heated in the Heat Exchanger to the temperature close to body temperature.

It should be noted that the power supply back-up functionality enabled by the Battery Unit 250 is only needed when dialysis treatment is being performed on a patient by the Dialysis Monitor and, consequently this functionality is not needed when no dialysis treatment is being performed.

As thermal disinfection and the starting up of preparation of treatment fluid are only carried out when no patient is connected to the Dialysis Monitor the energy stored in the Battery Unit 250 could be used (even to a point depleting the Battery Unit entirely) without any risk for a patient.

Figure 4:
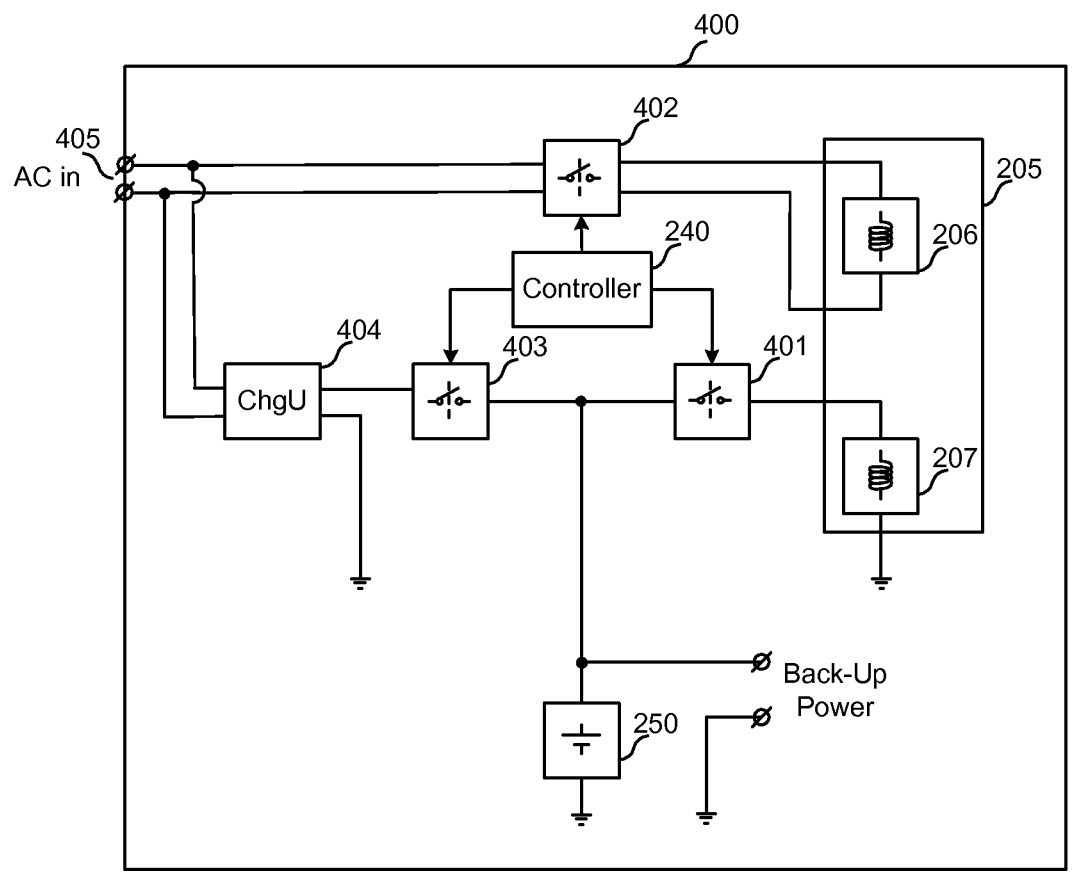
FIG. 4 shows a circuit diagram of an embodiment of the present invention.

FIG. 4 shows a circuit diagram of an embodiment of the present invention. As is illustrated in FIG. 4, the Battery Unit 250 is connected to an input of a First Switch 401. The output of the First Switch is connected to the Second Heating Element 207 of the Heater 205. As is illustrated by the arrow from the Controller 240 to the First Switch 401, the Controller 240 is operationally connected to the First Switch 401 such that the Controller 240 can control the states of the First Switch 401. In a first state (when the first switch is "closed"), energy will be provided from the Battery Unit 250 to the Second Heating Element 207. In this first state, the Second Heating Element 207 of the Heater 205 will heat the fluid in the Treatment Fluid Path, at least the fluid in the Tank and/or fluid in the vicinity of the Second Heating Element. In a second state (when the First Switch is "open"), energy will be prevented from being supplied from the Battery Unit 250 to the Second Heating Element 207. In this second state, the Second Heating Element 207 of the Heater 205 will no longer heat the fluid in the Treatment Fluid Path (in the Tank and/or fluid in the vicinity of the Second Heating Element). The Battery Unit 250 is configured to provide back-up power (at the connection point labelled "Back-Up Power" in FIG. 4) to at least a portion of the Dialysis Monitor at a time when the a patient is receiving dialysis treatment should the supply of external power be discontinued.

In the case of thermal disinfection, the user may initiate thermal disinfection by giving a command on the User Interface 101. The Controller 240 will then control the First Switch to enter its first state and the Second Heating Element 207 of the Heater 205 will heat the fluid in the Treatment Fluid Path. The heated fluid will be made to flow through the Treatment Fluid Path by the Controller 240 being programmed to control the Flow Pump 220 and the Suction Pump 226. This will result in thermal disinfection of the Treatment Fluid Path as discussed above. At the completion of the thermal disinfection, the Controller 240 controls the First Switch to enter its second state and the Second Heating Element 207 of the Heater 205 will no longer heat the fluid in the Tank and/or Treatment Fluid Path.

In the case of starting up the preparation of treatment fluid, the user may initiate the starting up by giving a command on the User Interface 101. The Controller 240 will then control the First Switch 401 to enter its first state and the Second Heating Element 207 of the Heater 205 will heat the fluid in the Treatment Fluid Path. The heated fluid will be made to flow through the Treatment Fluid Path by the Controller 240 being programmed to control the Flow Pump 220 and the Suction Pump 226. As the dialysis monitor is not performing dialysis treatment on a patient at this point of time, the treatment fluid is normally led from the upstream portion of the Treatment Fluid Path to the downstream portion of the Treatment Fluid Path by means of the Bypass Conduit 223 (with reference to FIG. 2) or through the Bypass Valve 301 (with reference to FIG. 3) which then is in a fluidly open state. In these cases, treatment fluid is not being provided to a dialyzer at the time of starting up the preparation of treatment fluid. Energy from the Battery Unit 250 is now provided to the Heater 205 and the temperature of the treatment fluid can quickly be increased to a suitable temperature (close to body temperature e.g. 37° C.). The Controller 240 may read the temperature as measured by the Treatment Fluid Path Temperature Sensor 219 and operates the First Switch 401 between the open and closed states based on the measured temperature in order to arrive at the suitable temperature (using an appropriate control algorithm, e.g. a PID algorithm). Before starting dialysis treatment on a patient, the Controller 240 controls the First Switch 401 to enter its second state and the Second Heating Element 207 of the Heater 205 will no longer heat the fluid in the Tank and/or Treatment Fluid Path.

In an alternative embodiment, which may be combined with other embodiments of the present invention, the dialysis monitor is equipped with a Second Switch 402 as is shown in FIG. 4. An input of the Second Switch 402 is connected to a Power Supply Inlet 405 and an output of the Second Switch 402 is provided to a First Heating Element 206 of the Heater 205. As is illustrated by the arrow from the Controller 240 to the Second Switch 402, the Controller 240 is operationally connected to the Second Switch 402 such that the Controller 240 can control the states of the Second Switch 402. In a first state (when the Second Switch 402 is "closed"), energy will be provided from the Power Supply Inlet 405 (assuming the Power Supply Inlet is connected to an external power source (not shown)) to the First Heating Element 206. In this first state, the First Heating Element 206 of the Heater 205 will heat the fluid in the Treatment Fluid Path, at least the fluid in the Tank (if any) and/or fluid in the vicinity of the First Heating Element. In a second state (when the Second Switch 402 is "open"), energy will be prevented from being supplied from the Power Supply Inlet 405 to the first Heating Element 206. In this second state, the First Heating Element 206 of the Heater 205 will no longer heat the fluid in the Treatment Fluid Path (in the Tank (if any) and/or fluid in the vicinity of the Second Heating Element).

In operation, after the user has initiate thermal disinfection, or initiated the starting up of the preparation of treatment fluid, by giving appropriate command(s) on the User Interface 101, as the case may be, the Controller 240 will control the First Switch 401 and the Second Switch 402 to enter their first states (closed) and the First Heating Element 206 and the Second Heating Element 207 of the Heater 205 will heat the fluid in the Treatment Fluid Path. The heating of the fluid in the Treatment Fluid Path (and in the Tank, if any) will occur quicker when power is provided both from the external power source and from the Battery Unit 250 to the Heater 205 at the same time. As a result, the thermal disinfection of the Treatment Fluid Path, or at least a portion thereof, or the starting up of the preparation of treatment fluid, as the case may be, will also be quicker and, as a consequence, the time between treatments can be shortened. Additionally, the overall power provided to the Heater 205 from the external power source and the Battery Unit may together surpass the power that can be delivered by the external power source solely. At the completion of the thermal disinfection, or the starting up of the preparation of treatment fluid, as the case may be, the Controller 240 controls the First Switch 401 and the Second Switch 402 to enter their second states (opened) and the First Heating Element 206 and the Second Heating Element 207 of the Heater 205 will no longer heat the fluid in the Treatment Fluid Path.

In alternative embodiments which may be combined with other embodiments of the present invention, the Controller 240 may control the First Switch 401 and the Second Switch 402 to enter their first states never, partly or wholly during the same time after the initiation of the thermal disinfection (e.g. in preparation for and/or at least partly during thermal disinfection of at least a portion of the Treatment Fluid Path), or the starting up of the preparation of treatment fluid, as the case may be.

In an alternative embodiment which may be combined with other embodiments of the present invention, a temperature sensor (not shown) may be located with the Heater 205 in a manner such that a signal representative of the temperature of the fluid in the Heater (or Tank, if any) is established. The temperature sensor is connected to the Controller 240 and the signal is read by the Controller as a temperature parameter. The temperature parameter can be used by the Controller 240 to control the First and the Second Heating Elements, 206 and 207, such that, for example, a maximum temperature (for example 95° C. in the case of thermal disinfection and 37° C. in the case of starting up the preparation of treatment fluid) of the fluid in the Heater 205 is not surpassed. In particular, the Controller 240 may control one or both of the First and Second Switches, 401 and 402, to enter its/their second state in order to prevent overheating of the Heater 205 or the fluid in the Tank.

In yet a further embodiment of the present invention, which may be combined with other embodiments of the present invention, the Dialysis Monitor is equipped with a Charger Unit 404 and a Third Switch 403 as is shown in FIG. 4. An input of the Charger Unit 404 is connected to the Power Supply Inlet 405 and an output of the Charger Unit 404 is connected to an input of the Third Switch 403. An output of the Third Switch 403 is connected to the Battery Unit 250. As is illustrated by the arrow from the Controller 240 to the Third Switch 403, the Controller 240 is operationally connected to the Third Switch 403 such that the Controller 240 can control the states of the Third Switch 403. In a first state (when the Third Switch 403 is "closed"), energy will be provided from the Charger Unit 404 (assuming the Charger Unit receives power from an external power source (not shown) connected to the Power Source Inlet 405) to the Battery Unit 250. In this first state, the battery/ies of the Battery Unit 250 will be charged. In a second state (when the Third Switch 403 is "open"), energy will be prevented from being supplied from the Charger Unit 404 to the Battery Unit 250. In this second state, the battery/batteries of the Battery Unit 250 will not be charged and the Charger Unit 404 will be disconnected from the input of the First Switch 401.

In operation, after the user has initiate thermal disinfection, or initiated the starting up of the preparation of treatment fluid, by giving appropriate command(s) on the User Interface 101, as the case may be, the Controller 240 will control the Third Switch 403 to enter its second state (opened) before it controls the First Switch 401 to enter its first state (closed). Conversely, after the Controller 240 has controlled the First Switch 401 to enter its second state (opened), the Controller 240 controls the Third Switch 403 to enter its first state (closed). As a result, the Charger Unit 404 will only be connected to the Battery Unit 250, and charge the same, during periods of time when the Battery Unit is not providing power to the Second Heating Element 207. The required power to drive the Second Heating Element 207 would normally be significant and by this design, the Charger Unit 404 does only have to be designed to provide the power of charging the Battery Unit 250 (and not to withstand the significantly higher power should it have been connected directly to the Second Heating Element 207). The Battery Unit 250 can be charged at any pace during dialysis treatment or during period of times when the Dialysis Monitor is not in operation (which could be for example during the night).

Even though the Power Supply Inlet 405 in FIG. 4 only has been illustrated to connect to the Third Switch 403 and the Charger Unit 404, it should be understood that the power supply received at the Power Supply Inlet 405 is used to provide power to the functional elements of the Dialysis Monitor in general as is known in the art.

Figure 5A:
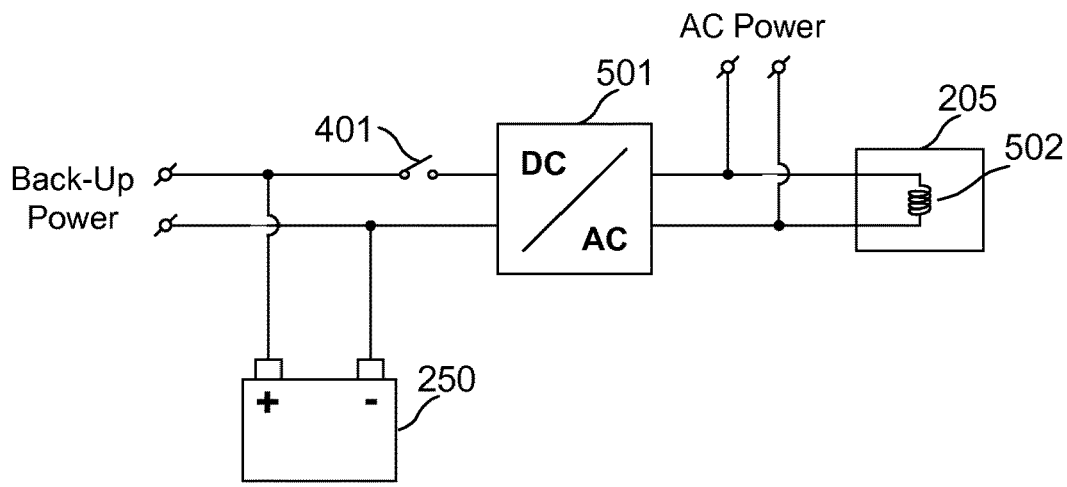
FIGS. 5a, 5b, and 5c show circuit diagrams of alternative embodiments of the present invention.
Figure 5B:
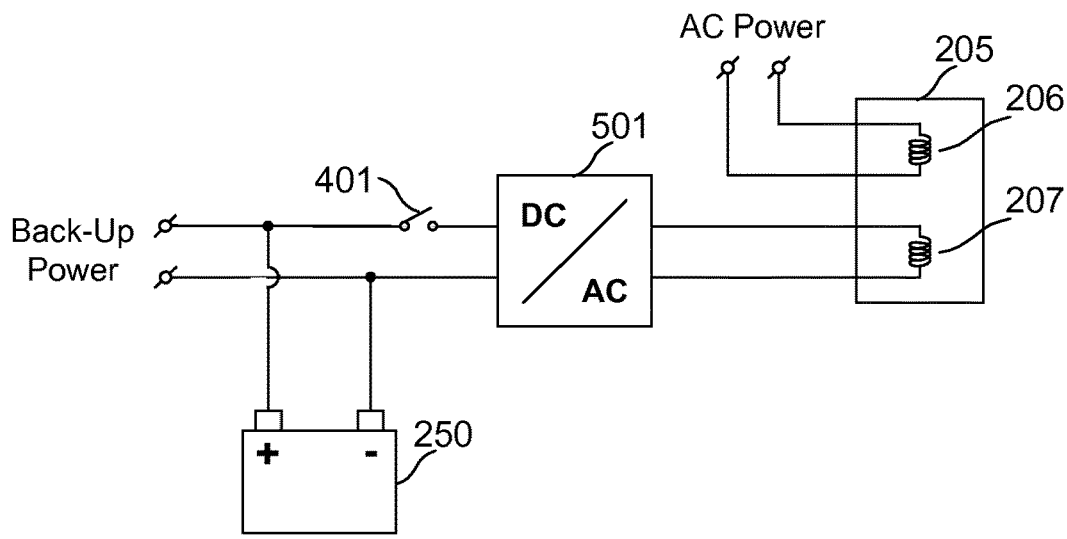
Figure 5C:
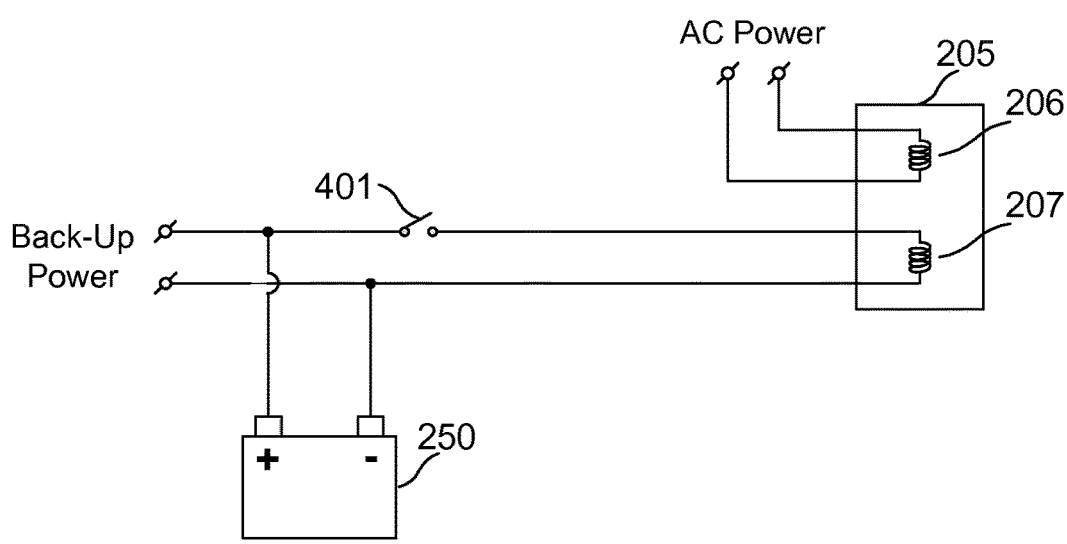

FIGS. 5a, 5b, and 5c show circuit diagrams of alternative embodiments of the present invention which may be combined with other embodiments of the present invention.

According to the embodiment shown in FIG. 5a the Battery Unit 250 provides DC Back-Up Power (labelled "Back Up Power" in the figure) to (parts of) the Controller 240 and other elements of the Dialysis Monitor as may be controlled by the Controller. The First Switch 401 (which is controlled by the Controller), when in closed state, connects the Battery Unit 250 to the DC input of a DC/AC Converter 501. The AC output of the DC/AC Converter is connected in parallel to the AC Power (labelled "AC Power" in the figure) which provides power to a Common Heating Element 502 of the Heater 205.

According to the embodiment shown in FIG. 5b the Battery Unit 250 provides DC Back-Up Power (labelled "Back Up Power" in the figure) to (parts of) the Controller 240 and other elements of the Dialysis Monitor as may be controlled by the Controller. The First Switch 401 (which is controlled by the Controller), when in closed state, connects the Battery Unit 250 to the DC input of a DC/AC Converter 501. The AC output of the DC/AC Converter is connected to the Second Heating Element 207 of the Heater 205 whereas the AC Power (labelled "AC Power" in the figure) provides power to the First Heating Element 206 of the Heater 205.

According to the embodiment shown in FIG. 5c the Battery Unit 250 provides DC Back-Up Power (labelled "Back Up Power" in the figure) to (parts of) the Controller 240 and other elements of the Dialysis Monitor as may be controlled by the Controller. The First Switch 401 (which is controlled by the Controller), when in closed state, connects the Battery Unit 250 to the Second Heating Element 207 of the Heater 205 whereas the AC Power (labelled "AC Power" in the figure) provides power to the First Heating Element 206 of the Heater 205.

In variations to the embodiments discussed in relation to FIG. 4 or FIG. 5, the Heater 205 may be replaced or combined with the Second Heater 305 (if present). In these cases the First Heating Element 206 may be replaced or combined with the First Heating Element of the Second Heater 306 and the Second Heating Element 207 may be replaced or combined with the Second Heating Element of the Second Heater 307. In further variations to these embodiments, the First Heating Element 206 may be connected in series with, or parallel to, the First Heating Element of the Second Heater 306. Similarly, the Second Heating Element 207 may be connected in series with, or parallel to, the Second Heating Element of the Second Heater 307.

In an alternative embodiment, which may be combined with other embodiments of the present invention, the Heater 205 is not attached to a tank but rather directly heat fluid in the Treatment Fluid Path (that is, operating as an in-line heater).

In an alternative embodiment, which may be combined with other embodiments of the present invention, the first heating element 206 and the second heating element 207 may be located in separate heaters (not shown). Similarly, the First Heating Element of the Second Heater 306 and the Second Heating Element of the Second Heater 207 may be located in separate heaters (not shown).

In an alternative embodiment, which may be combined with other embodiments of the present invention, the Dialysis Monitor receives treatment fluid from an external source (e.g. centrally prepared (not shown) for the entire clinic or hospital, or from a bag (not shown)). With reference to FIG. 2 and FIG. 3, in this embodiment, the Treatment Fluid Mixing Unit 210 is then not required and can be left out.

In the disclosed embodiment the terminology "switch" has been used to illustrate the invention (also shown symbolically as a switch in FIG. 4 and in FIGS. 5a, 5b, and 5c). It should be understood that the "switch" may be made up of one or a number of thyristor(s), triac(s), diac(s), diode(s), relay(s), transistor(s), and any kind of driver circuit(s), or a combination thereof.

The Controller 240 may comprise analogue electronic circuits and/or at least one microprocessor with related data-bus connected to at least one memory device (semiconductor memory, hard-disc drive, USB-memory, etc), communication devices, etc, wherein the memory is provided with software code which adapts/configures the at least one microprocessor to carry out one, several, or all of the various operations and methods of the embodiments discussed above.

An advantage of at least some embodiments of the present invention is that the power provided to the Heater by means of the external power supply and the Battery Unit may exceed the maximum power available from the external power supply, which in turn, leads to a quick heating of the fluid to be used for thermal disinfection of the Treatment Fluid Path or heating of the treatment fluid when starting up the preparation of treatment fluid.

Another advantage, at least in respect of some embodiments of the present invention, is that thermal disinfection of the Dialysis Monitor can be achieved in a short period of time. This in turn makes the time-between-treatments shorter since the time-between treatment is dependent on the time required for thermal disinfection. The short period of time is achieved by the use of the Battery Unit, possibly combined with power from the electrical system (external power supply/mains), for heating fluid to be used during thermal disinfection.

Yet another advantage, at least in respect of some embodiments of the present invention, is that starting up the preparation of treatment fluid can be achieved in a short period of time. This in turn makes the time-between-treatments shorter since the time-between treatment is dependent on the time required to starting up the preparation of treatment fluid. The short period of time is achieved by the use of the battery unit for heating fluid to a suitable temperature (close to body temperature e.g. 37° C.).

Consequently, there is the advantage of a more efficient use of the Dialysis Monitors (e.g. measured in percentage of time available for dialysis treatment of patients at for example clinics and hospitals). The working hours of the operating staff (nurses and technicians, as the case may be, who operate the dialysis monitors) can be shortened which in turn has positive economic effects for the clinics/hospitals and also positive work environmental effects for the operating staff. Patients also benefit as the Dialysis Monitors are used more efficiently.

The invention claimed is:

1. A dialysis monitor for performing dialysis treatment on a patient, said dialysis monitor comprising:
   a treatment fluid path configured to provide treatment fluid to a dialyzer when dialysis treatment is performed by the dialysis monitor;
   a heater configured to heat fluid present in the treatment fluid path;
   a battery unit configured to provide back-up power to at least a portion of the dialysis monitor during treatment should a supply of external power be discontinued;
   a first switch connected between the battery unit and the heater, said first switch having a first state where energy is supplied from the battery unit to the heater and a second state where energy is prevented from being supplied from the battery unit to the heater; and
   a controller programmed
      (i) to use the battery unit to provide back-up power to at least the portion of the dialysis monitor should the supply of external power be discontinued during treatment, and wherein the controller is further programmed such that during discontinued external power (a) treatment fluid flowing through the dialyzer is stopped while blood flows through the dialyzer, or (b) at least one pump is stopped and at least one extracorporeal blood transport line is clamped to prevent blood from being extracted from the patient; and
      (ii) to control a state of said first switch and to set the state of said first switch to said first state, thereby supplying energy from the battery unit to the heater, at a time when dialysis treatment is not being performed on the patient by the dialysis monitor.

2. The dialysis monitor according to claim 1, wherein the controller is programmed to set the state of said first switch to said first state at a time of preparing for and/or at least partly during thermal disinfection of at least a portion of the treatment fluid path thereby using energy from the battery unit for heating fluid used for thermal disinfection.

3. The dialysis monitor according to claim 1, wherein the controller is programmed to set the state of said first switch to said first state at a time when the dialysis monitor is starting up a preparation of treatment fluid thereby using energy from the battery unit for heating fluid towards and/or to a temperature to be used during dialysis treatment.

4. The dialysis monitor according to claim 1, wherein the controller is programmed to set the state of said first switch to the first state at a time when treatment fluid is not being provided to the dialyzer.

5. The dialysis monitor according to claim 1, wherein the controller is programmed to set the state of said first switch to said second state, thereby preventing energy from being supplied from the battery unit to the heater, when the patient is receiving dialysis treatment.

6. The dialysis monitor according to claim 1, wherein the heater comprises at least a first heating element and a second heating element, the first heating element configured to receive energy from an external power source and the second heating element configured to receive energy from said battery unit.

7. The dialysis monitor according to claim 1, wherein said heater comprises a first heater and a second heater, wherein the first heater is configured to receive energy from said battery unit, and said second heater is configured to receive energy from an external power source.

8. The dialysis monitor according to claim 1, wherein the dialysis monitor further comprises a second switch connected between an external power source and the heater, and wherein the controller is programmed to control the second switch to, in a first state, provide energy from the external power source to the heater and, in a second state, prevent energy to be provided from the external power source to the heater.

9. The dialysis monitor according to claim 8, wherein the controller is programmed to provide energy from the battery unit to the heater at least partly during a same time as energy is provided from the external power source to the heater.

10. The dialysis monitor according to claim 1, wherein the dialysis monitor further comprises:
a charger unit electrically connected to the battery unit; and
a third switch connected between an external power source and the battery unit,
wherein the controller is programmed to control the third switch to, in a first state, enable energy from the charger unit to charge the battery unit and, in a second state, to prevent energy from the charger unit to charge the battery unit.

11. The dialysis monitor according to claim 10, wherein the controller is programmed to control the third switch to prevent energy from the charger unit to charge the battery unit when the controller is programmed to control said first switch to enter said first state and thereby supply energy from the battery unit to the heater.

12. The dialysis monitor according to claim 1, which includes:
a treatment fluid pump;
the dialyzer; and
a blood circuit configured to circulate blood between the patient and the dialyzer,
wherein the treatment fluid pump pumps the treatment fluid through the treatment fluid path to the dialyzer.

13. The dialysis monitor according to claim 1, wherein during (i), when external power is discontinued during treatment, the battery unit provides power to enable the controller to place the dialysis monitor in a patient safe mode.

14. The dialysis monitor according to claim 13, wherein the controller in the patient safe mode (a) stops the treatment fluid from flowing through the dialyzer while blood flows through the dialyzer or (b) stops at least one pump and clamps at least one extracorporeal blood transport line to prevent blood from being extracted from the patient.

15. A dialysis monitor for performing a dialysis treatment on a patient, said dialysis monitor comprising:
a treatment fluid path configured to provide treatment fluid to a dialyzer when dialysis treatment is performed by the dialysis monitor;
a heater configured to heat the treatment fluid;
a battery unit configured to provide back-up power to at least a portion of the dialysis monitor during treatment should a supply of external power be discontinued;
a switch located between the battery unit and the heater, the switch having a first state in which energy is supplied from the battery unit to the heater and a second state in which energy is prevented from being supplied from the battery unit to the heater; and
a controller programmed such that (i) back-up power is provided from the battery unit to at least the portion of the dialysis monitor should the supply of external power be discontinued during treatment, wherein the battery unit provides power to enable the controller to place the dialysis monitor in a patient safe mode, and the controller in the patient safe mode (a) stops the treatment fluid from flowing through the dialyzer while blood flows through the dialyzer or (b) stops at least one pump and clamps at least one extracorporeal blood transport line to prevent blood from being extracted from the patient; and (ii) the switch is set to the first state, thereby allowing energy to be supplied from the battery unit to the heater, at a time when dialysis treatment is not being performed.

16. The dialysis monitor of claim 15, wherein the controller is programmed to cause the switch to allow energy to be supplied from the battery unit to the heater at a time when dialysis treatment is not being performed, regardless of whether external power from the supply is provided or discontinued.

17. The dialysis monitor according to claim 15, wherein the heater comprises at least a first heating element and a second heating element, the first heating element configured to receive energy from an external power source and the second heating element configured to receive energy from said battery unit.

18. The dialysis monitor according to claim 17, wherein the said heater comprises a first heater and a second heater, wherein the first heater is configured to receive energy from said battery unit, and said second heater is configured to receive energy from an external power source.

* * * * *